US012685802B2

(12) United States Patent
Murphy et al.

(10) Patent No.: US 12,685,802 B2
(45) Date of Patent: Jul. 21, 2026

(54) REGENERATIVE TISSUE AND NATURAL TISSUE IMPLANTS

(71) Applicant: Vascudyne Inc, Plano, TX (US)

(72) Inventors: Richard F. Murphy, White Bear Township, MN (US); Kemal Schankereli, Stillwater, MN (US); Mark Lauren, Buffalo, NY (US)

(73) Assignee: Vascudyne, Inc., St. Paul, MN (US)

(*) Notice: Subject to any disclaimer, the term of this patent is extended or adjusted under 35 U.S.C. 154(b) by 716 days.

(21) Appl. No.: 16/627,285

(22) PCT Filed: Jun. 30, 2018

(86) PCT No.: PCT/US2018/040510
§ 371 (c)(1),
(2) Date: Dec. 28, 2019

(87) PCT Pub. No.: WO2019/006430
PCT Pub. Date: Jan. 3, 2019

(65) Prior Publication Data
US 2020/0129667 A1 Apr. 30, 2020

Related U.S. Application Data

(60) Provisional application No. 62/678,954, filed on May 31, 2018, provisional application No. 62/528,000, filed on Jun. 30, 2017.

(51) Int. Cl.
*A61L 27/36* (2006.01)
*A61L 27/22* (2006.01)
*A61L 27/24* (2006.01)

(52) U.S. Cl.
CPC ......... *A61L 27/3641* (2013.01); *A61L 27/225* (2013.01); *A61L 27/227* (2013.01);
(Continued)

(58) Field of Classification Search
CPC .. A61L 27/3641; A61L 27/225; A61L 27/227; A61L 27/24; A61L 27/3604;
(Continued)

(56) References Cited

U.S. PATENT DOCUMENTS 6,666,886 B1 12/2003 Tranquillo et al.
7,264,632 B2 9/2007 Wright et al.
(Continued)

FOREIGN PATENT DOCUMENTS

AU 2014268778 A1 * 11/2015 ......... C08B 37/0075
EP 1278559 3/2008
(Continued)

OTHER PUBLICATIONS

Baptista et al., "Whole organ decellularization—a tool for bioscaffold fabrication and organ bioengineering," Annu Int Conf IEEE Eng Med Biol Soc, 2009, 2009:6526-9, 4 pages.
(Continued)

*Primary Examiner* — Suzette J Gherbi
(74) *Attorney, Agent, or Firm* — Fish & Richardson P.C.

(57) ABSTRACT

The present invention is an improved implant made from regenerative tissue or natural tissue, methods of making the implant, and methods of using the implant.

8 Claims, 3 Drawing Sheets

(52) U.S. Cl.
CPC ........... *A61L 27/24* (2013.01); *A61L 27/3604* (2013.01); *A61L 27/3633* (2013.01); *A61L 27/3687* (2013.01); *A61L 27/3691* (2013.01)

(58) Field of Classification Search
CPC ............. A61L 27/3633; A61L 27/3687; A61L 27/3691; A61L 27/3683; A61L 27/38; A61L 27/50; A61L 27/507; A61L 27/3679
See application file for complete search history.

(56) References Cited

U.S. PATENT DOCUMENTS

| | | | |
|---|---|---|---|
| 8,192,981 B2 | 6/2012 | Hoerstrup et al. | |
| 8,198,245 B2 | 6/2012 | Niklason et al. | |
| 8,382,822 B2 | 2/2013 | Pavcnik et al. | |
| 8,399,243 B2 | 3/2013 | Bouten et al. | |
| 8,465,758 B2 * | 6/2013 | Lewis | A61P 43/00 424/422 |
| 8,617,237 B2 | 12/2013 | Hoerstrup et al. | |
| 8,636,793 B2 | 1/2014 | Hoerstrup et al. | |
| 8,795,357 B2 | 8/2014 | Yohanan et al. | |
| 9,034,333 B2 | 5/2015 | Brokopp et al. | |
| 9,126,199 B2 | 9/2015 | Moritz et al. | |
| 9,127,242 B2 | 9/2015 | Guertin et al. | |
| 9,375,513 B2 | 6/2016 | Sun et al. | |
| 9,556,414 B2 | 1/2017 | Dahl et al. | |
| 9,650,603 B2 | 5/2017 | Dahl et al. | |
| 9,657,265 B2 | 5/2017 | Dahl et al. | |
| 10,213,307 B2 | 2/2019 | Dwork et al. | |
| 10,413,411 B2 | 9/2019 | Dwork | |
| 10,617,519 B2 * | 4/2020 | Vidlund | A61F 2/2418 |
| 11,338,063 B2 * | 5/2022 | Daniel | A61L 27/3675 |
| 11,589,982 B2 * | 2/2023 | Tranquillo | A61F 2/2412 |
| 11,786,366 B2 * | 10/2023 | Vidlund | A61B 17/0643 623/2.11 |
| 2003/0004149 A1 * | 1/2003 | Roskelley | C07D 209/86 514/183 |
| 2003/0228692 A1 | 12/2003 | Goldstein et al. | |
| 2003/0229394 A1 | 12/2003 | Ogle et al. | |
| 2004/0115176 A1 | 6/2004 | Swartz et al. | |
| 2004/0206363 A1 | 10/2004 | McCarthy et al. | |
| 2005/0186672 A1 * | 8/2005 | Mahadeorao | A61P 27/02 435/368 |
| 2006/0153815 A1 | 7/2006 | Seyda et al. | |
| 2006/0210597 A1 | 9/2006 | Hiles | |
| 2006/0246584 A1 | 11/2006 | Covelli | |
| 2006/0259137 A1 * | 11/2006 | Artof | A61F 2/243 623/2.11 |
| 2006/0286664 A1 | 12/2006 | McAllister et al. | |
| 2007/0061800 A1 | 3/2007 | Cheng et al. | |
| 2007/0178588 A1 | 8/2007 | McAllister et al. | |
| 2007/0269789 A1 | 11/2007 | Covelli et al. | |
| 2007/0293932 A1 * | 12/2007 | Zilla | A61F 2/856 623/1.53 |
| 2009/0062907 A1 | 3/2009 | Quijano et al. | |
| 2009/0254175 A1 | 10/2009 | Quijano et al. | |
| 2009/0319003 A1 | 12/2009 | Castel et al. | |
| 2011/0020271 A1 | 1/2011 | Niklason et al. | |
| 2011/0224779 A1 | 9/2011 | Schankereli | |
| 2012/0046731 A1 | 2/2012 | von Oepen et al. | |
| 2012/0046739 A1 | 2/2012 | von Oepen et al. | |
| 2012/0230950 A1 | 9/2012 | Niklason et al. | |
| 2013/0013083 A1 * | 1/2013 | Blum | A61L 27/60 623/23.7 |
| 2013/0197622 A1 | 8/2013 | Mitra et al. | |
| 2013/0204356 A1 | 8/2013 | Dwork et al. | |
| 2013/0218253 A1 * | 8/2013 | Kaufmann | A61L 31/146 623/1.2 |
| 2013/0282111 A1 | 10/2013 | Dwork | |
| 2013/0345824 A1 * | 12/2013 | Dahl | A61F 2/04 435/68.1 |

| | | | |
|---|---|---|---|
| 2014/0035805 A1 | 2/2014 | Minnen et al. | |
| 2014/0052247 A1 * | 2/2014 | Daniel | A61L 27/3604 623/23.72 |
| 2014/0058496 A1 | 2/2014 | Tranquillo et al. | |
| 2014/0330377 A1 | 11/2014 | Niklason et al. | |
| 2014/0356331 A1 | 12/2014 | Badylak et al. | |
| 2015/0012083 A1 | 1/2015 | Dahl et al. | |
| 2015/0037436 A1 | 2/2015 | Huang et al. | |
| 2015/0088247 A1 | 3/2015 | L'Heureux et al. | |
| 2015/0182664 A1 | 7/2015 | Ayares et al. | |
| 2015/0202063 A1 * | 7/2015 | Soletti | A61L 27/44 623/1.15 |
| 2015/0305860 A1 | 10/2015 | Wang et al. | |
| 2016/0067741 A1 * | 3/2016 | Weiss | A61L 27/22 427/384 |
| 2016/0158007 A1 | 6/2016 | Centola et al. | |
| 2016/0203262 A1 | 7/2016 | Sheehy et al. | |
| 2017/0014230 A1 | 1/2017 | Pellegrini et al. | |
| 2017/0027694 A1 | 2/2017 | Dwork | |
| 2017/0056175 A1 | 3/2017 | Chin et al. | |
| 2017/0135805 A1 | 5/2017 | Dahl et al. | |
| 2017/0224478 A1 | 8/2017 | Savage et al. | |
| 2017/0273784 A1 | 9/2017 | Racchini et al. | |
| 2017/0296323 A1 | 10/2017 | Engelmayr et al. | |
| 2017/0306292 A1 | 10/2017 | Dahl et al. | |
| 2018/0110617 A1 | 4/2018 | Howard et al. | |
| 2018/0243071 A1 * | 8/2018 | Eigler | A61F 2/2487 |
| 2019/0239879 A1 * | 8/2019 | Zilla | A61F 2/07 |
| 2020/0060814 A1 * | 2/2020 | Murphy | A61F 2/2418 |
| 2023/0270919 A1 * | 8/2023 | Gerecht | A61L 27/507 623/1.41 |
| 2023/0397981 A1 * | 12/2023 | Rocco | D04B 21/16 |
| 2023/0397985 A1 * | 12/2023 | Von Oepen | A61F 2/2418 |

FOREIGN PATENT DOCUMENTS

| | | |
|---|---|---|
| WO | WO 2004/018008 | 3/2004 |
| WO | WO 2004/101012 | 11/2004 |
| WO | WO 2007/025233 | 3/2007 |
| WO | WO 2007/092902 | 8/2007 |
| WO | WO 2010/120539 | 10/2010 |
| WO | WO 2017/064667 | 4/2017 |

OTHER PUBLICATIONS

Crapo et al., "An overview of tissue and whole organ decellularization processes," Biomaterials, Apr. 2011, 32(12):3233-43, 23 pages.
Extended European Search Report in European Appln. No. 17877212.5, dated Nov. 17, 2020, 10 pages.
Extended European Search Report in European Appln. No. 18824613.6, dated Mar. 5, 2021, 6 pages.
International Preliminary Report on Patentability in International Appln. No. PCT/US2017/064559, mailed Jun. 13, 2019, 7 pages.
International Preliminary Report on Patentability in International Appln. No. PCT/US2018/040510, mailed Dec. 31, 2019, 8 pages.
International Search Report and Written Opinion in International Appln. No. PCT/US2017/064559, mailed Mar. 7, 2018, 13 pages.
International Search Report and Written Opinion in International Appln. No. PCT/US2018/040510, mailed Dec. 6, 2018, 14 pages.
Office Action in European Appln. No. 18824613.6, dated Sep. 13, 2022, 5 pages.
Ott et al., "Perfusion-decellularized matrix: using nature's platform to engineer a bioartificial heart," Nat. Med., Feb. 2008, 14(2):213-21.
Syedain et al., "Implantable arterial grafts from human fibroblasts and fibrin using a multi-graft pulsed flow-stretch bioreactor with noninvasive strength monitoring," Biomaterials, Jan. 2011, 32(3):714-22, 17 pages.
U.S. Appl. No. 16/466,023, filed Jun. 1, 2019, Richard F. Murphy.
U.S. Appl. No. 18/256,867, filed Jun. 9, 2023, Richard F. Murphy.

* cited by examiner

10

11

12

14

13

15

REGENERATIVE TISSUE AND NATURAL TISSUE IMPLANTS

I. FIELD OF THE INVENTION

The invention relates to an implant comprising a regenerative tissue (RT) matrix material, and a method for manufacturing an implant comprising this matrix material. The disclosure further relates to a both RT and natural coronary artery bypass grafts, among other implants.

This invention relates also to tissue vascular grafts, e.g., coronary artery bypass grafts and to peripheral grafts, their method or preparing, and their use. This invention also relates to processes of preparing heterogeneous graft material from regenerative tissue or animal tissue.

II. BACKGROUND OF THE INVENTION

A relatively new field of medicine—since the early 1990s—is the field of Regenerative Medicine. Regenerative Medicine is the process of creating living and functional tissues to repair, replace, or restore tissue or organ structure and function lost due to age, disease, damage, or congenital defects. This field of medicine uses new methods including (stem) cell therapy, development of medical devices and tissue engineering.

The use of prepared heterogenous graft material for human surgical implantation is well known. More specifically, the use of treated animal tissue as human tissue grafts, replacement valves, and similar implantation surgical procedures is well known. However, problems of immunogenicity, thrombogenicity, calcification, material strength, and size have not been adequately addressed in the prior art.

While the use of cattle or other meat supplying animals ensures an adequate supply of tissue for processing, a combination of (i) the lower natural collagen levels and higher non-collagenous protein levels in the tissue of older animals, (ii) the lack of a processing step to effectively remove non-collagenous proteins, and (iii) the limitations of "wet" cross-linking, when used alone, to bond glutaraldehyde with collagen molecules, results in a product that still exhibits traits of antigenicity, thrombogenicity and calcification that can result in post-surgical complications, as well as limited endothelialization properties.

More specifically, the use of glutaraldehyde alone in chemical cross-linking of tissue results in a tissue sample in which the release of glutaraldehyde after implantation of the sample results in an increased risk of inflammation in and around the implanted tissue.

Since the 1930's, medical researchers have attempted to develop suitable natural and synthetic alternatives for obtaining small diameter grafts useful in vascular surgery. Historically, attempts to fabricate such tubular grafts from man-made materials have been somewhat unsuccessful. Homologous tissues, however, are not always readily available, and are not always readily available in the size the surgeon needs. Furthermore, some of these tissues may be immunogenic and therefore may require processing or certain treatments to reduce their immunogenicity.

One of the problems encountered, for both natural and synthetic grafts, is producing a small diameter graft, e.g., less than about 6 mm internal diameter. For small diameter grafts made of heterologous or synthetic material, as the diameter of the graft decreases, the opportunity for blockage increases due to the inherent thrombogenicity of such materials. Moreover, for all grafts of a small diameter, as the size decreases, the sutureability and flexibility of the graft may decrease, both characteristics that are highly desirable in a suitable graft material. For these and other reasons, the conventional grafts are typically 6 to 10 mm (an intermediate size graft) or greater than 10 mm (a large graft).

Notwithstanding the usefulness of the above-described methods, a need still exists for increasing patency; making an implant less thrombotic in structure and/or function; minimizing calcification; and increasing the useful life of the implant.

III. SUMMARY OF THE INVENTION

One embodiment of the invention is the preparation and use of RT to make implants and their use as implants. This aspect of the invention is an implant produced from RT, including but not limited to coronary or peripheral grafts; processes for making RT; processes of using RT and RT implants; and methods of treatment using RT implants.

Another embodiment of the invention provides a process for preparing a bioprosthetic material or natural graft material for use in surgical procedures on mammals.

An advantage of both embodiments of the invention is the starting material itself.

The biological materials according to the present invention, are processed to modify (e.g., reduce or eliminate) calcification characteristics, resorbability, size and shape, thinness, collagen content, and other characteristics and properties that will become clear from the description of the invention. The methods, uses, and products of the present invention are intended for implant in a mammal, preferably a human. All of the biological materials, processed according to the present invention, are appropriate for use in an in vivo environment, and include one or more of the following desirable properties for graft material suitable for implantation: a) size compatibility with surrounding vessels to which it will be anastomosed; b) sutureability, kink resistance, softness, radial and longitudinal compliance, and flexibility (a softer hand); c) non-thrombogenicity or low levels of thrombogenicity; d) durability; e) ease of sterilization; f) readily available, and available in diameters and lengths appropriate for surgical procedures; g) shelf life appropriate for market conditions (typically greater than three years); h) resistant to infection; i) sufficient strength to resist aneurysm formation; j) non-immunogenic; k) resistant to degradation; and l) resistant to formation of neointimal hyperplasia.

Moreover, materials processed according to the present invention are flexible, that is they retain what is called by one skilled in the art as a pliable "hand." This is a relatively subjective term referring to how the processed biological material feels when it is handled. In the present context, hand refers to flexibility, ease of manipulation, ease of handling as part of a surgical procedure, and a biological material that is not overly rigid.

Accordingly, the present invention provides methods of producing small diameter vascular prostheses, and the products produced by the process.

The present invention also provides a method for preparing small diameter vascular prosthesis suitable for implantation in the human body.

Although specific advantages have been enumerated above, various embodiments may include some, none, or all of the enumerated advantages.

Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

With the following enabling description of the drawings, the apparatus should become evident to a person of ordinary skill in the art.

IV. BRIEF DESCRIPTION OF THE FIGURES

V. DETAILED DESCRIPTION OF THE INVENTION

Figure 1:
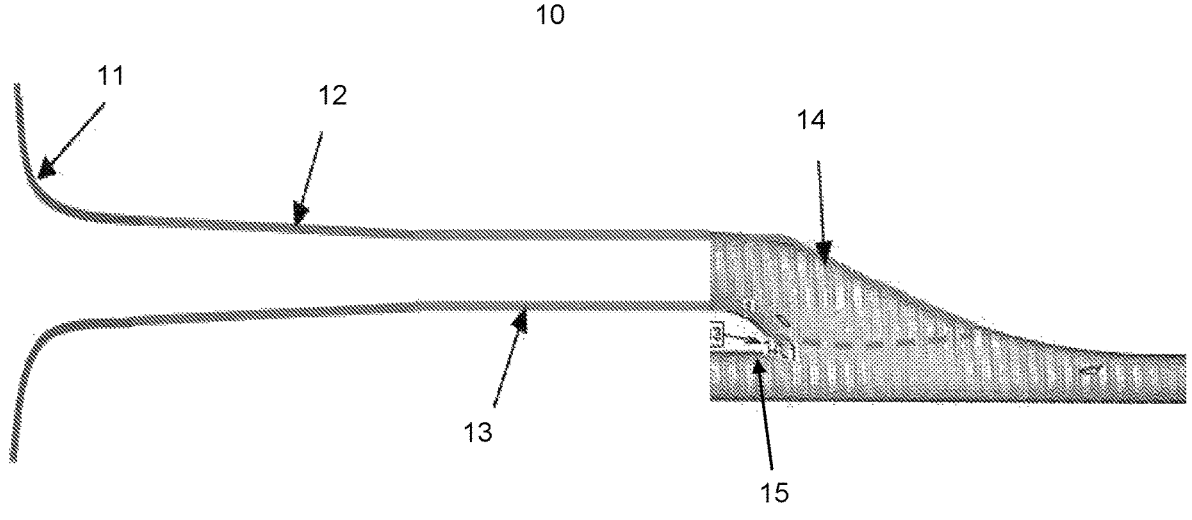
FIG. 1 shows an exemplary mandrel used to shape a tissue graft of the present invention.

The present invention is a graft or prosthesis formed from regenerative tissue. The invention includes methods of making the tissue and methods of making the graft or prosthesis.

The present invention is also a graft, tube, conduit, or sheet, including but not limited to a coronary artery bypass graft. The graft may be formed by culturing ECM-producing cells in the presence of fibrinogen and thrombin under conditions that permit the formation of regenerative tissue.

The present invention is also a method of producing or forming the graft, tube, conduit, or sheet.

The present invention is also the use of the graft, tube, conduit, or sheet as a prosthesis, preferably an implantable prosthesis.

The present invention is also the use of regenerative tissue, as defined and produced herein, to treat a human or animal disease or condition, including but not limited to cardiovascular diseases and disorders; vascular disease and disorders; and any disease and disorder that may benefit from catheter-based or supplied prosthetics or processes.

In accordance with the present invention, any prosthesis may be formed using ergative tissue (RT) or engineered tissue. Engineered tissue, as used herein, refers to tissue formed or processed as disclosed in the following, 2007/061800; WO 2007/092902; 2016/0203262; WO/2004/018008; WO 2004/101012; U.S. Pat. Nos. 8,192,981; 8,399,243; 8,617,237; 8,636,793; 9,034, 333; 9,126,199; U.S. Ser. No. 10/523,618; U.S. Ser. No. 10/556,959; U.S. Ser. No. 13/771,676; 2015/ 0012083; 2009/0319003; 2011/0020271; 2012/ 0230950; 2013/0013083; 2014/0330377; 2014/ 035805; 2017/0135805; 2017/0296323; 2017/ 0306292; U.S. Pat. Nos. 8,198,245; 9,127,242; 9,556, 414; 9,657,265; and 9,650,603; all of which are hereby incorporated in the entirety be reference.

In one embodiment of the invention, the bioengineered tissue may be made according to U.S. Patent Application 2014/0058496 (Tranquillo, et al.), incorporated in its entirety be reference. Any process or method for producing engineered tissue is included within the scope of the present invention.

The present invention also is the use of the tissue as an implant. Suitable uses include but are not limited to coronary artery bypass graft (CABG), a valve leaflet, a peripheral graft, a sling, bulking agents, prolapsed bladder repair, stented or stentless pericardial valve replacement, stented or stentless pulmonic valve replacement, transcatheter valve prosthesis, aortic bioprosthesis/valve replacement or repair, annuplasty rings, bariatric surgery, dural patching, enucleation wraps, gastric banding, herniation repair, lung surgery e.g. lung volume reduction, peripheral arterial or venous valve replacement, pericardial patching, rotator cuff repair, uretheral slings, valve repair, vascular patching, valve conduit insertion, or arterial conduit insertion.

The regenerative tissue (RT) of the present invention, is processed to modify (e.g., reduce or eliminate) calcification characteristics, resorbability, size and shape, thinness, collagen content, and other characteristics and properties that will become clear from the description of the invention.

The methods, uses, and products of the present invention are intended for implant in a mammal, preferably a human.

All of the RT, processed according to the present invention, are appropriate for use in an in vivo environment, and include one or more of the following desirable properties: a) size compatibility with surrounding vessels to which it will be anastomosed; b) sutureability, kink resistance, softness, radial and longitudinal compliance, and flexibility (a softer hand); c) non-thrombogenicity or low levels of thrombogenicity; d) durability; e) readily available, and available in diameters and lengths appropriate for surgical procedures; f) shelf life appropriate for market conditions (typically greater than three years); g) resistant to infection; h) sufficient strength to resist aneurysm formation; i) non-immunogenic; j) resistant to degradation; and k) resistant to formation of neointimal hyperplasia.

The RT of the present invention is distinct from certain other kinds of regenerative or engineered tissue in the use of crosslinked fibrinogen that is later degraded during the culturing process. Also, the RT of the present invention can be contracted and the fibers aligned, partially due to fibrin having no or little resistance to contraction that occurs naturally as part of the collagen/ECM formation process. Furthermore, the RT of the present invention does not include any synthetic materials, as is typical in other processes that use PLA or PGA or the like.

A product and/or method of the present invention typically includes combining fibrinogen or fibrinogen-like material, thrombin, and matrix-producing cells to produce a fibrin gel with a homogeneous cell suspension. In preferred embodiments of the invention, the cell infused fibrin gel undergoes casting, used herein to refer to encapsulating cells in a fibrin gel, and culturing to form the collagenous tissue or grafts. IN other preferred embodiments, the tissue or graft may be allowed to contract, preferably in a controlled manner. In accordance with the present invention, the process permits customized or optimized fiber alignment during the contraction phase. Customized or optimized alignment includes, but is not limited to radial alignment, longitudinal alignment, both radial and longitudinal alignment, and a pre-determined ratio of radial and longitudinal alignment.

One or more methods of the present invention may also include molding or forming the cell-seeded fibrin gel into [a pre-determined] shape; manipulating, mechanically, the tissue in the presence of culture medium to produce RT; and decellularizing the RT.

By making the tissue manipulation device from a nonadherent material or a material that binds cells only weakly, such as stainless steel or ePTFE, the tissue manipulation device can be removed without damaging the tissue.

Each of these ingredients and steps will now be described in more detail.

Cell Source

Cells or a cell line of the present invention is any cell or line that produces an extracellular matrix (ECM). Matrix-producing cells include, but are not limited to fibroblasts, embryonic stem cells, post-natal stem cells, adult stem cells, mesenchymal cells, interstitial cells, endothelial cells, smooth or skeletal muscle cells, myocytes (muscle stem cells), chondrocytes, adipocytes, fibromyoblasts, and ecto-dermal cells, including ductile and skill cells, hepatocytes, Islet cells, cells present in the intestine and other parenchy-mal cells, and osteoblasts and other cells forming bone or cartilage.

Fibrinogen Source

Any source of fibrinogen may be used. Fibrinogen is typically used in the present invention in a buffer. In preferred embodiments, the fibrinogen is mixed into Hepes buffer.

Thrombin Source

Any source of thrombin may be used. Thrombin is typically used in the present invention in a buffer and conventional cell culture medium. In preferred embodi-ments, the thrombin is mixed into Hepes buffer and DMEM.

In the most preferred embodiments, the thrombin solution also includes a clot formation factor or co-factor, such as a source of calcium. The preferred source of calcium is CaCl2.

Media

The separated cells are typically suspended in a high protein medium (e.g., media with fetal bovine serum or human serum (including autologous serum)), pelleted by centrifugation and plated onto tissue culture plates. Fibro-blasts, for example, typically attach to the tissue culture plate before other cells, thereby giving rise to a population of fibroblast cells. The resulting population of fibroblasts cells are typically substantially homogenous, but may con-tain additional cell types including macrophages, endothelial cells, epithelial cells, and the like, present in the tissue from which the fibroblasts are isolated. The fibroblasts are then grown, optionally in the presence of or contacting the form or mold.

One or more matrix-producing cells may be cultured in any nutrient, growth, or maintenance medium. Any cell culture medium may be used. A preferred medium is Eagle's minimal essential medium; a most preferred medium is DMEM (Dulbecco's modified Eagle's medium).

During growth in culture the cells may be cultured with agents that promote cellular proliferation and growth. Such agents include a number of growth factors that can be selected based upon the tissue to be grown and the cell types present (e.g., keratinocyte growth factor (KGF); vascular endothelial cell growth factor (VEGF); platelet derived growth factor (PDGF); fibroblast growth factor (FGF); a transforming growth factor (TGF) alpha, beta, and the like; insulin; growth hormone; somatomedins; colony stimulating factors; erythropoietin; epidermal growth factor; hepatic erythropoietic factor (hepatopoietin); and liver-cell growth factor to name a few, others are known in the art). Serum, such as fetal bovine serum (FBS) or the like, can also provide some of these growth factors. In addition, agents such as ascorbic acid and/or insulin can be used to increase extracellular matrix production or to promote collagen growth.

Exemplary media or nutrients include but are not limited to one or more of the following: L-ascorbic acid or a phosphate derivative of L-ascorbate acid (e.g. Asc 2-P); serum; and growth factors, Dulbecco's Modified Eagle's Medium.®. (DMEM), DMEM F12 Medium.®., Eagle's Minimum Essential Medium.®., F-12K Medium.®., Iscove's Modified Dulbecco's Medium.®., RPMI-1640 Medium.®, insulin, and/or ascorbic acid.

An exemplary cell suspension medium (e.g., before cast-ing) is DMEM with Hepes.

An exemplary cell suspension medium after casting is DMEM with a growth factor supplement, preferably con-taining a serum albumin such as bovine serum albumin (BSA). Exemplary serum includes but is not limited to fetal bovine serum (FBS) or fetal calf serum (FCS) or formulated FBS substitutes such as Fetal Clone I, Fetal Clone II, Fetal Clone III, or the like, or a combination of any or all. In preferred embodiments of the invention, the cell suspension medium after casting also includes insulin and ascorbic acid.

After gel formation and an initial incubation period, the graft may be incubated in a growth or maintenance medium. This medium is typically supplemented with a medium such as FBS, and may optionally include one or more antibiotics, or growth factor. The preferred growth/maintenance medium is DMEM with FBS (about 5% to about 40% concentration) and antibiotic is a penicillin/streptomycin combination (sometimes referred to as "penstrep"). The medium may be changed and/or supplemented periodically as need. For example, this medium may be supplemented with formulated FBS substitutes, reduced FBS concentra-tions, insulin, and/or ascorbic acid.

In most cell culture applications, adherent cell cultures can only be maintained for a few days to a few weeks before the individual cells release from a substrate. The addition of agents that promote cell growth, viability and/or adhesion can be used during the culture process. For example, addi-tion of agents such as ascorbic acid, retanoic acid, and copper can be used to increase the production of extracel-lular matrix proteins thereby generating a more robust tissue sheet of cells. Moreover, by treating the cell culture surface/ substrate with extracellular matrix proteins or other factors (e.g., a protein such as gelatin or fibrin), adhesion can be prolonged.

The introduction of one or more tissue manipulation device(s)s (e.g., a plurality of control rods) can be used to hold down the edges of the tissue on a culture container, form, or substrate, thus preventing spontaneous graft or tissue/material detachment. These devices or elements may also be used to control or limit tissue contraction. The rods or tissue manipulation device can be designed such that they generate clamping forces (e.g., via gravity, magnetic forces and the like) to effectively secure the sheet. Moreover, the rods can be made of a biocompatible material such as ePTFE (e.g., an ePTFE outer surface and a metallic core) or stainless steel that will be slightly adherent to the cells present in a tissue sheet. In this manner, once a tissue sheet is removed from the culture surface it can be handled easily.

Decellularization

The cultured cells are then decellularized using any process that results in a decellularized RT. As used herein decellularized refers to a construct that is decellularized such that it is substantially acellular, immune-resistant, and/or calcification resistant. Preferably, the construct is substan-tially acellular comprising less than 2% cells, less than 1% cells or contains no cells. The cells are intact cells. The cells can be living cells or dead cells. Exemplary processes include but are not limited to: WO 2007/025233; WO 2010/120539; Ott, et al (2008, Nat. Med., 14:213-21);

Baptista, et al. (2009, Conf. Proc. IEEE Eng. Med. Biol. Soc., 2009:6526-9); or Crapo, et al., (2011, Biomaterials, 32:3233-43).

In another aspect, a tissue or material of the invention is substantially decellularized to provide extracellular matrix materials provided by the population of cells. In some cases, it may be advantageous to decellularize or denature all or part of the tissue or tissue engineered construct. A decellularized tissue may have a reduced level of immunogenicity, as well as other attributes. Decellularizing or denaturing the tissue may also enhance the mechanical characteristics of the tissue or construct. The tissue may be decellularized, denatured, or chemically modified using a variety of techniques. In the simplest embodiment, the tissue can be air-dried or lyophilized to kill the cells. Thermal shock, acoustic treatment, changes in pH, osmotic shock, mechanical disruption, or addition of toxins can also induce cell death or apoptosis. Similarly, the tissue can be cross-linked or fixed using agents such as paraformaldehyde. Other treatments to decellularize or denature the tissue are possible using radiation, detergents (SDS or triton ×100), enzymes (RNAase, DNAase), or solvents (alcohol, acetone, or chloroform). These techniques are only some of the examples of techniques to decellularize, denature or chemically modify all or part of the tissue and are not meant to limit the scope of the invention. Treatment with hypotonic and/or hypertonic solutions, which have non-physiological ionic strengths, can promote the decellularization process. Proteases also can be used effectively to decellularize tissue. The decellularization can be performed in stages with some or all of the stages involving differential treatments. For example, a potent mixture of proteases, nucleases and phospholipases could be used in high concentrations to decellularize the tissue. The decellularized extracellular matrix may then have applied another tissue layer or another decellularized sheet.

The RT of the present invention may be characterized by one or more of the following: oriented fibers; thickness up to about 1 mm, preferably between about 100 μm and about 500 μm; non-immunogenic or minimally immunogenic; a tissue, sheet or shape that is anisotropic; a sheet or shape that is suitable for cutting into shapes, e.g., by scalpel, die, or laser; suppleness; suturability; no or little calcification during life of implant; crosslink density, or variations of crosslink density through the material thickness; collagen concentration; collagen density, or variation of crosslink density through the material thickness; remodeling proclivity; absorption; resorption; degradability, regions of greater stiffness; and regions of greater flexibility.

In preferred embodiments of the invention, the RT has oriented fibers leading to suture pull-out resistance, anisotropic material properties as witnessed by tensile strength, even more preferably, adapted for its end use (e.g., a sheet, or a tube, or a valve).

Various Method Steps:

Without intending to be limited to a particular process for producing RT, an exemplary method includes combining fibrinogen or the like, thrombin or the like, and extracellular matrix (ECM)-producing cells; and allowing the cells to grow sufficiently to produce ECM. One skilled in the art will recognize that up to nine cell passages typically optimizes ECM production. In preferred embodiments, the result is cells in a degradable suspension or gel.

The mandrel, shape, or form may be formed from a lubricious substance, or may be coated with a lubricious substance (e.g., teflon or pluronic acid); and the suspension/gel may be coated on the mandrel. In preferred embodiments of the invention, the lubricious substance is a nonionic surfactant, such as pluronic acid.

In some embodiments of the invention, two opposing ends of the mandrel may include a slidable anchor (e.g., mesh) or the like that controls the time and amount of contraction of the gel. It has been found that as the tissue/suspension/gel contracts in a controlled fashion, fibers may orient in a certain direction. While on the form or substrate, the gel containing cells may be nourished by adding nutrient, growth, and/or maintenance medium, any or all of which may be chosen to promote ECM production.

Mechanical manipulations include, for example, static culture on a form (such as a isodiametric or non-isodiametric mandrel, glass sheet, or glass rod) which, for a non-adhesive mandrel, leads to circumferential alignment as the cells compact the gel, causing the axial length to shorten, and circumferential stretching or distension while providing for axial shortening to maintain the circumferential alignment. Generally, such stretching or distortion may be cyclic or periodic. See, for example, Syedain et al., 2011, Biomaterials, 32:714-22. Simply by way of example, mechanical manipulations of the cell-seeded gel as it is remodeled into a cell-produced extracellular matrix can be performed using flow-stretch or pulsed flow-stretch methods in any number of bioreactors.

In an embodiment of the present disclosure, the implant, the fibers (of the matrix material) have a preferred orientation direction. Preferably, the fibers in the implant are arranged in such a way that when the implant is implanted, the fibers are arranged substantially perpendicular to the blood stream. Preferably, the preferred fiber alignment is circumferential around an imaginary axis of the implant wherein the axis points in the direction of blood flow in case of a tubular implant.

By mimicking the extra cellular matrix of the natural environment, a tissue can be grown having good structural properties, which eventually develop towards a native-like architecture (i.e., the tissues of the present invention are a biomimetic material).

Some embodiments of the invention may further include storing and/or sterilizing a medical device of the present invention. These embodiments may include preselected storage solution; preselected sterilization solution or technique; storage packaging; and/or sterilization packaging.

The RT may in turn be used to make a skirt, leaflets, a valve, or a coating or layer on medical devices intended for implantation. The RT of this embodiment may be used in any body lumen, including but not limited to an artery, a vein, or any body lumen that passes a body fluid (e.g., a ureter or a urethra). The present invention also is the use of the tissue as an implant. Suitable uses include but are not limited to coronary artery bypass graft (CABG), a valve leaflet, a peripheral graft, a sling, bulking agents, prolapsed bladder repair, stented or stentless pericardial valve replacement, stented or stentless pulmonic valve replacement, transcatheter valve prosthesis, aortic bioprosthesis/valve replacement or repair, annuplasty rings, bariatric surgery, dural patching, enucleation wraps, gastric banding, herniation repair, lung surgery e.g. lung volume reduction, venous valve replacement, pericardial patching, rotator cuff repair, uretheral slings, valve repair, vascular patching, valve conduit insertion, or arterial conduit insertion.

Preferred embodiments of the invention include a medical device or prosthesis of the present invention packaged and ready to use by the surgeon or in the operating room.

Verification Protocols

One or more attributes of the RT or process conditions can be tested, determined, or evaluated using convention testing techniques. These verification protocols include, but are not limited to: visual observation and/or by product or process testing. Visual observation includes but is not limited to translucence, e.g., the tissue becoming more opaque and/or thicker. Product and process testing includes but is not limited to collagen content; tensile strength or modulus (in one or more directions, e.g., longitudinal or circumferential); suture retention (in one or more directions); histology; shrink temperature; acellular content; and thickness.

The present disclosure further relates to a method for growing a graft, comprising the step of providing an implant, preferably an implant according to the present disclosure to a subject (a patient). The implant is preferably an implant according to the present disclosure. This step can be preceded by the step of making an incision in the skin of the subject. In some embodiments of the invention, the graft is substantially isodiametric in a middle portion, shaped on one or both ends. In more preferred embodiments, the graft has at least one larger diameter end portion.

Some embodiments of the invention may include a degradable scaffold that can be seeded by extracellular matrix producing cells. The scaffold may be formed from fibrin, PLA, PGA, or other synthetic or biological polymer, and mixtures thereof. The ECM producing cells can be cultured with the scaffold, allowing the cells to produce ECM, which can in turn replace the degradable scaffold. Optionally, the scaffold can be manipulated or processed (as described herein) to create alignment of the fibers in the ECM (e.g., an anisotropic matrix). The final product, preferably in the form of a sheet, may be decellularized using detergents, dehydrated (e.g., freeze drying), or fixed/cross-linked (e.g., glutaraldehyde fixation) to create a sheet of engineered tissue with or without cells.

Alternatively, the present invention is a process for preparing a natural tissue graft comprising the steps of: 1) selecting an animal tissue specimen and harvesting it; 2) cleaning the harvested tissue; 3) in some embodiments (or optionally), digesting the cleaned tissue; 4) surface treating the digested tissue; 5) forming the surface treated into a predetermined shape; 6) and crosslinking the formed tissue. Typically, the cross-linked graft may then be sterilized and/or packaged according to known methods.

The present invention also is a natural tissue graft produced by a process of the present invention.

The present invention also is the use of the graft as an implant. Suitable uses include but are not limited to coronary artery bypass graft (CABG) and a peripheral graft.

In preferred embodiments of the invention, the natural tissue graft is shaped, formed, or configured on a mandrel or form.

In some preferred embodiments of the invention, the natural tissue is processed dynamically, e.g., is pulsed or tumbled, during the crosslinking step.

The present invention also is a surgical kit comprising one or more of the following: a regenerative tissue implant or graft processed or produced according to the present invention; a natural tissue graft processed or produced in accordance with the present invention; one or more instruments for implanting the graft; a rinse tray; a rinse solution, e.g., heparin; and suture material.

The biological material may be derived from different animal species, typically mammalian. Suitable sources include, but are not limited to, bovine, porcine, equine, ovine, kangaroo, rabbit, boar, bear, and human. Although autologous biological materials may be used, the preferred material is non-autologous. In some embodiments of the invention, the biological material may be naturally produced or genetically engineered, and explanted from the source. Also, the source of the biological material may be a genetically engineered species specifically designed to produce tissue having one or more pre-determined attributes, e.g., lower immunogenicity, or tissue that requires minimal fixation or anti-calcification processing.

In other embodiments, the biological material may be grown or seeded, with or without an appropriate matrix or backing, preferably a biodegradable matrix. In these embodiments of the invention, the biological material is grown or cultured using well known in vitro culture techniques, typically in a bioreactor or the like. In some embodiments of the invention, the biological material may be produced by implanting an object, such as a mandrel or the like, for a time sufficient to become encapsulated by a layer of tissue. This tissue may be harvested, processed, and used according to the present invention. For the purpose of some embodiments of the invention, the term biological material will also encompass synthetic and/or mechanical material which are sometimes used to reinforce or supplement collagen-containing materials.

Alternatively, the predetermined tissue specimen is taken from a bovine animal 30 days old or less. In one preferred embodiment, the tissue specimen is taken from an animal that is not more than about 10 days old, and in a preferred embodiment about 5 days old. In preferred embodiments of the invention, the tissue is taken from a bobby calf.

The harvested tissue specimen is a collagen-based tissue selected from the group consisting of pericardium, dura mater, blood vessels, fascia, pleura tissue, and any duct or tube that can be processed according to the present invention. In a preferred embodiment of the invention, the tissue specimen is a ureter.

The choice of a ureter is specifically advantageous because it may be obtained from a conventional source; is tubular shaped without any side branches; is typically long (e.g., up to about 120 cm, typically about 90 cm) and suitable for cutting into 80 to 90 cm lengths (or shorter); tends to be naturally isodiametric; has sufficient mitogens present, a feature that has been found to contribute to superior or desired compliance and longevity under typical use conditions; and can be easily shaped. The harvested biological material is typically packed in cold saline (e.g., 0.9% NaCl) until ready for further processing.

In some embodiments of the invention, the finished graft may be between about 20 and about 60 cm in length. The invention also includes attaching one or more (typically two) grafts together to form a longer finished graft. Not intending to be limited to a certain length, these grafts may be about 40 to about 120 cm in length.

The harvested tissue then needs to be cleaned. A process of the present invention includes any cleaning and/or rinsing step. These are very well known to those skilled in the art. For example, the harvested tissue may first be mechanically, enzymatically, or detergent cleaned to remove extraneous matter. Various harvesting and cleaning protocols are well known by those skilled in the art. Typically, harvested materials are kept cool until processing, and ideally processing should be initiated within twenty-four (24) hours of harvesting. Primarily, gross adventitia, muscle tissue, and fat are removed.

The harvested biological material may then be treated to remove all non-collagenous, non-elastin tissue, thereby leaving a collagenous, elastic tubular substrate. Various digestion steps are well known to those skilled in the art, and may be used in a process according to the present invention. For example, soaking the structure in a bioactive agent detergent, such as 1% sodium dodecyl sulfate (SDS), for about 24 to 72 hours at room temperature is sufficient to remove all or most of the non-collagenous, non-elastin material. At this point, the structure is typically yellow-white and has a soft hand.

The digested tissue may then be surface treated. In accordance with the present invention, surface treatment refers to altering the surface charge of the tissue so that the surface is net negatively charged. Various surface treatment processes are well known to those skilled in the art and may be used in the present invention. A preferred method of the present invention is succinylation, e.g., binding a succinate to the surface. In preferred embodiments of the invention, the natural tissue graft is a ureter having a net negative surface charge.

The surface treated material is then formed into a predetermined shape. Shaping may occur by mounting the material on a mandrel of predetermined shape and size, typically in the range from about 2 to about 6 mm diameter, preferably less than 6 mm.

In accordance with preferred embodiments of the invention, pre-determined shape refers to any forming or shaping the natural tissue into any shape or form that mediates or improves the hemodynamic function of the graft or its tissue reaction when it is implanted. These hemodynamic functions typically refer to blood flow dynamics within the graft after it is implanted. These dynamics include but are not limited to promoting laminar blood flow, reducing turbulence, minimizing shear at the anastomosis site, and/or protecting the bed of the recipient artery.

In accordance with the present invention, the mandrel is any shape that shapes the body of the graft and/or one of more ends of the material into a desired shape. The Figures provide examples of various shapes that have been found to be advantageous. In most preferred embodiments of the invention, at least one end of the material is shaped into a cuff. In another preferred embodiment of the invention, the material may be shaped, e.g., like a funnel, to match the contact angle of the artery or vein at the implant site. In some embodiments of the invention, the graft may be tapered along its length.

In a most preferred embodiment of the invention the mandrel and the corresponding shape of the graft is configured to match or compliment the contact angle of the recipient artery when the graft is implanted.

An exemplary mandrel is shown in FIG. 1. Mandrel 10 comprises a proximal end 11 that may be various shaped. As illustrated, proximal end 11 is flared. A portion 12 of the mandrel may be tapered along its length. Another portion 13 may be of fixed diameter along its length. Distal end 14 may be shaped to match the anastomosis site. In the illustrated embodiment, lead in angle 15 is preferably between about 10 degrees and 30 degrees, intended to promote laminar flow in the outflow tract.

Figure 2:
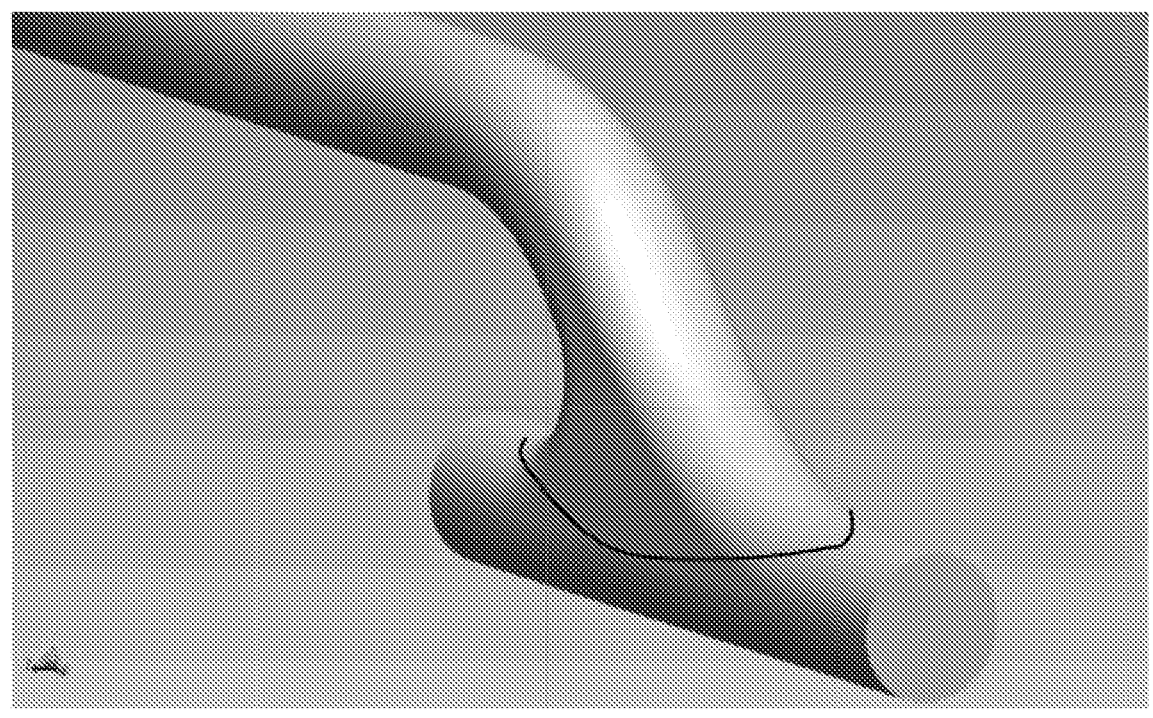
FIG. 2 is an angled view of the distal end of an exemplary mandrel.
Figure 3:
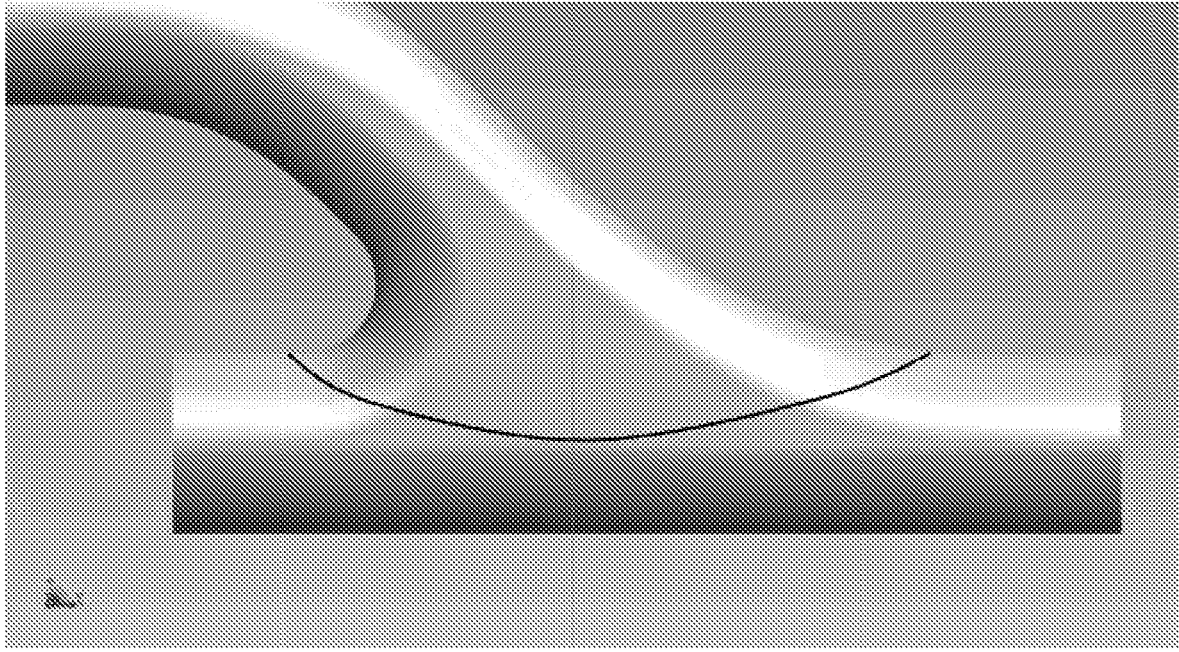
FIG. 3 is a side and close-up view of the distal end in FIG. 2.

FIGS. 2 and 3 provide other views of the distal end of an exemplary mandrel.

Figure 4:
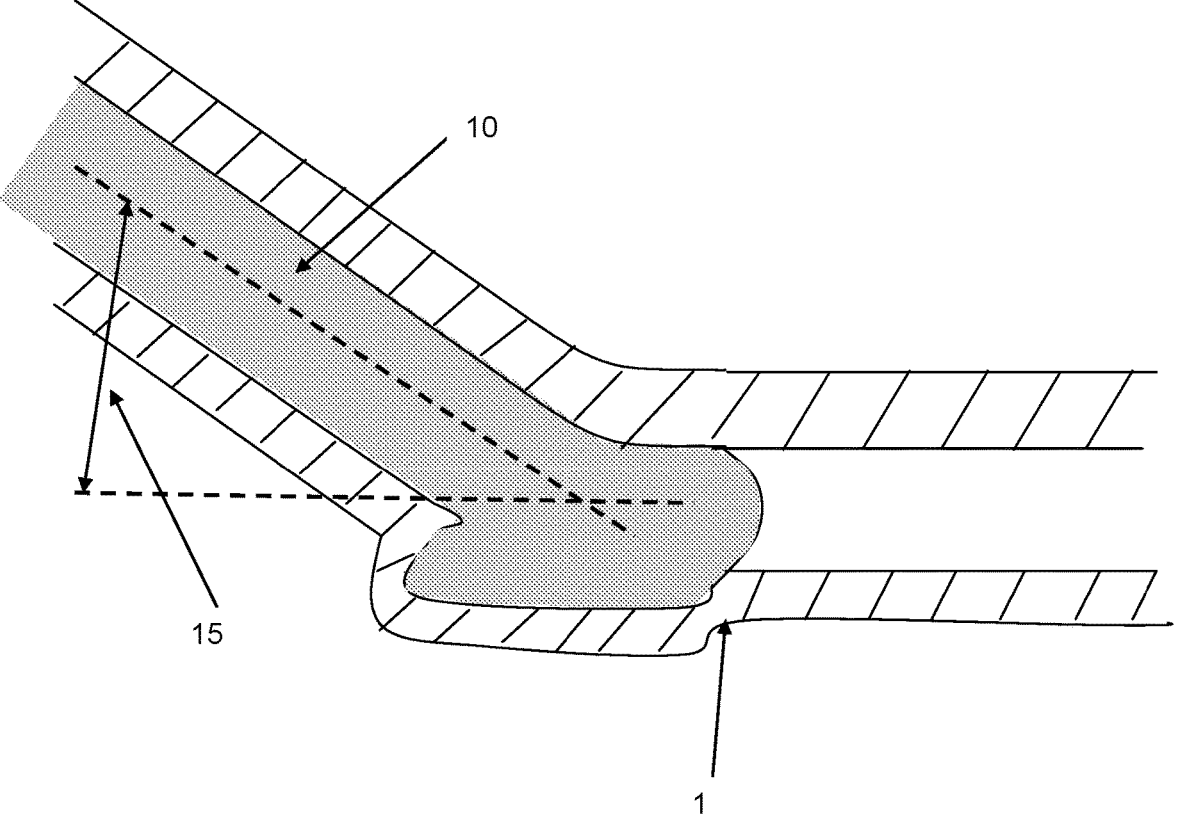
FIG. 4 shows a tissue positioned on a mandrel for shaping in accordance with the present invention.

FIG. 4 shows the natural tissue 1 positioned on a mandrel 10 of the present invention.

The mandrel may also be a balloon to facilitate removal after crosslinking.

The shape of the graft may be isodiametric, fully tapered, or partially tapered. As shown in FIG. 1, a graft may include a portion that is tapered and a portion that is isodiametric.

The tubular substrate natural tissue is next exposed to a suitable crosslinking agent. Mounting the tissue on a mandrel and then treating the tissue with a crosslinking agent may be used in combination so that the finished graft retains its desired or pre-determined shape. The preparation of biological material prior to implantation typically includes treatment to stabilize it against subsequent in vivo enzymatic degradation, and to reduce the intrinsic calcification, typically by crosslinking molecules, particularly collagen, on and in the tissue. Various aldehydes have been used for this purpose, including glyoxal, formaldehyde, and glutaraldehyde. Glutaraldehyde, however, is the agent of choice. In addition to fixing the tissue, glutaraldehyde is a good sterilizing agent and reduces the antigenicity of the tissue. To date, glutaraldehyde is the primary effective crosslinking agent for preparing tissues for implantation that can be used at physiologic pH under aqueous conditions.

Crosslinking biological materials, particularly using a glutaraldehyde solution, is very well known to those skilled in the art. Many such methods are described in the prior art. Generally, the crosslinking step comprises immersing the tissue in a reagent solution for from a few minutes to several days depending upon the desired degree of crosslinking. The solution may include one or a number of crosslinking reagents, such as, for example, glutaraldehyde, formaldehyde, glyoxal, diamine, and/or dialdehyde starch. The rate of crosslinking reaction can be controlled by controlling the concentration of crosslinking reagent and, to a lesser extent, by controlling the pH and/or the temperature of the crosslinking reagent. For example, the concentration of glutaraldehyde may be from about 0.001% to 8.0% volume to volume (v/v). Preferably, the concentration of glutaraldehyde is about 0.10% or greater.

In a preferred embodiment of the present invention, the biological material may be compressed when positioned on the mandrel and flexed during the crosslinking step. One skilled in the art will recognize that the tissue may be crosslinked dynamically. The inventors believe that crosslinking dynamically leads in part to a natural tissue graft having a softer hand and improved hemodynamics.

As used herein, "dynamically" refers to movement, e.g., the opposite of static. One skilled in the art will recognize that dynamic manipulation may take many forms, including but not limited to compressing, flexing, altering conditions, vibrating, mixing, shaking, and the like.

In preferred embodiments of the invention, the RT may be processed or formed using one or more tissue manipulation devices, some of which are described in U.S. Publication No. US 2007/0178588, filed Dec. 14, 2006, and incorporated by reference in its entirety.

In accordance with the invention, one skilled in the art will recognize that certain parameters in the crosslinking protocol may be varied according to achieve a particular purpose. These parameters include, but are not limited to glutaraldehyde concentration and solution composition, pH and ionic strength, time and temperature of biological tissue exposure to glutaraldehyde, the ratio of tissue mass to volume of solution, and the biological tissue configuration during the initial fixation.

The graft material is then removed from the mandrel, washed to remove traces of the glutaraldehyde.

Once the cross-linking step has been completed, the tubular graft is removed from the mandrel and, if desired, may be subjected to an additional treatment in which the interior wall of the graft is coated with a drug, such as Heparin. It is believed that such processing enhances the biocompatibility of the graft with adjacent tissues and reduces the potential for formation of thrombi.

The tissue is placed over a shaping mandrel prior to crosslinking, and is crosslinked while on the mandrel to fix the shape.

The biological material may then be sterilized, following any sterilizing protocol e.g., by electron beam, gamma radiation, or the like. In a preferred embodiment of the invention, the biological material is sterilized by utilizing a liquid chemical sterilant consisting of 2% glutaraldehyde, or 75% ethanol and 2% propylene oxide at room temperature for approximately two weeks.

In accordance with the present invention, the anti-calcification step and sterilization may be combined into a single process step by using ethanol and propylene oxide. This combination sterilizes the tissue and is also responsible for providing anti-calcific properties to the graft.

Following that, the tubular graft is sterilized, using wet chemical treatment. Finally, once the sterilization step is completed, the prosthesis is ready for packaging in sterile solution, such as propylene oxide, for shipment and sale.

One of the embodiments of the present invention is a sterile closed package containing a biological material of the present invention. Typically, a separate container would hold individual or multiple samples having known size or dimensions. If desired, the biological material in the sterile package can be attached to another material or structure, such as an annuplasty ring, a sewing cuff, or a support for positioning the biological material on a stapler.

The biological material may then be placed or packaged in a container. In accordance with a preferred embodiment of the invention, the biological tissue is packaged and sealed in a bacteriostatic solution, typically in 1% propylene oxide, in its final container. Packaging preferably means placing the processed biological material in a container suitable for storage and/or shipping.

By using the process steps of the present invention, tubular vascular graft tissue is obtained having lumen of less than 6 mm in diameter which exhibits strength, sutureability, and softer hand so as to better match the compliance of the prosthesis to that of the ultimate host and reduce or eliminate intimal hyperplasia.

In a preferred embodiment of the invention, a natural tissue prosthesis is formed using the processes described above, where the tissue is provided in sterile form and is adapted to be implanted into a human or animal body and attached in place.

An example of a tissue graft of the present invention is a CABG, typically from about 2 mm to about 4 mm in internal diameter, and less than about 30 cm in length.

Another example of a tissue graft of the present invention is a peripheral graft, typically from about 3 mm to about 6 mm in internal diameter, and about 80 cm in length.

In a most preferred embodiment of the invention the CABG graft or the peripheral graft includes one or more ends that are shaped and sized to better fit an anastomized artery nor vein. For example, either of these grafts may comprise a distal tip that is cuff shaped. See, for example, FIG. 4.

Methods of use include using the tissue configured to an appropriate shape as replacement tissue for any of the following surgical purposes: stented or stentless pericardial valve replacement, stented or stentless pulmonic valve replacement, transcatheter valve prosthesis, aortic bioprosthesis/valve replacement or repair, annuplasty rings, bariatric surgery, dural patching, enucleation wraps, gastric banding, herniation repair, lung surgery e.g. lung volume reduction, peripheral arterial or venous valve replacement, pericardial patching, rotator cuff repair, uretheral slings, valve repair, vascular patching, valve conduit insertion, or arterial conduit insertion.

In accordance with preferred embodiments of the invention, pre-determined shape refers to any forming or shaping the natural tissue into any shape or form that mediates or improves the hemodynamic function of the graft or its tissue reaction when it is implanted. These hemodynamic functions typically refer to blood flow dynamics within the graft after it is implanted. These dynamics include but are not limited to promoting laminar blood flow, reducing turbulence, minimizing shear at the anastomosis site, and/or protecting the bed of the recipient artery.

In some embodiments, the invention is a prosthesis uses regenerative tissue formed into a graft, wherein said graft is formed into pre-determined shape. An exemplary shape is a tube or conduit, preferably hollow, or strawed shaped. In preferred embodiments, the tube has two ends and a central portion, and in the most preferred embodiments, the central portion is non-isodiametric in relation to one or both ends. For example, the central portion could be isodiametric and one or both ends of the tube could be a different shape, e.g., flared or cut. In some embodiments of the invention, at least one end of said prosthesis or tube is shaped into a cuff shape, including but not limited to the shapes shown in the Figures.

DEFINITIONS

The following definitions are used in reference to the invention:

(A) "Bobby calf" as used herein means a male or a female calf of a cow that is slaughtered before weaning, usually not more than 30 days from birth, and usually within one week of birth. BC animals are primarily used for the production of veal, meaning that a large and steady supply of tissue from such animals is available. BC pericardial tissue is known to be extremely thin, typically in the range of 0.005" to 0.007" (0.1270 mm to 0.1778 mm). Pericardial tissue from such animals also has a very high natural collagen content, providing the tissue both high strength and a variety of biocompatibility benefits, including low antigenicity, thrombogenicity and calcification potential; high endothelialization; high suture retention; and high bursting strengths. As the animal ages, the natural collagen content of its tissue decreases, and these biocompatibility benefits also decrease.

(B) "Cross-links" are bonds that link one polymer chain to another. They can be covalent bonds or ionic bonds. "Polymer chains" can refer to synthetic polymers or natural polymers, including proteins such as collagen. Examples of some common crosslinkers are the dimethyl suberimidate, formaldehyde and glutaraldehyde. Each of these crosslinkers induces nucleophilic attack of the amino group of lysine and subsequent covalent bonding via the crosslinker.

(C) As used herein, "decellularization" refers to the process of removing cells from a blood vessel, such that the three-dimensional structure of the extracellular matrix (ECM) scaffold remains. Physical methods and chemical and biologic agents are used in combination to lyse cells, often followed by a rinsing step to remove cell remnants and debris. Effective decellularization is dictated by factors such as tissue density and organization, geometric and biologic properties desired for the end product, and the targeted clinical application. Decellularization of blood vessels with preservation of the ECM integrity and bioactivity can be optimized by those skilled in the art, for example, by choosing specific agents and techniques during processing.

A variety of decellularization processes may be used. An exemplary process is described in U.S. Publication No. 2007/0178588, incorporated herein by reference.

As indicated herein, a decellularized vessel consists essentially of the extracellular matrix (ECM) components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures. Preferably, but not necessarily, residual cell debris also has been removed from the decellularized organ or tissue.

(D) As used herein, biomimetics or biomimicry refer to imitating the models, systems, and elements of nature for the purpose of solving complex human or animal problems. In the present invention, biomimetics is used for therapeutic purposes.

EXAMPLES

Example 1. Casting Protocol

Reagents:
20 mM Hepes; CaCl2), in 20 mM Hepes; fibrinogen; thrombin; 5% pluronic acid; DMEM w/Hepes; DMEM w/FBS; insulin; and ascorbic acid.
Method:
Coat form (e.g., mandrel; mold; tube; glass plate or rod) with a lubricous substance, e.g., pluronic acid solution.
If tissue contraction or stabilization is needed, prepare the devices or elements needed to stop or control contraction. These devices or elements may include restrictors or elements that resist or prevent the tissue from contracting, or allow controlled or limited contraction.
Harvest cells.
Mix fibrinogen solution (fibrinogen stock in 20 mM Hepes).
Mix thrombin solution (thrombin stock in DMEM w/Hepes and CaCl2) solution; as used herein, the first medium, or any medium suitable for suspending cells).
Suspend cells in the first medium formulation without FBS or serum supplement.
Add cell suspension to fibrinogen solution.
Add thrombin solution to cell suspension/fibrinogen solution; do not move for about 5 minutes, then transfer to incubator and incubate to allow gel to solidify (e.g., for about 30 minutes). As used herein, a graft is formed or begins to form as soon as the clotting reaction begins, typically within about one to two minutes after the cell/fibrinogen solution is mixed with the thrombin solution.
Supplement culture media DMEM base with FBS, P/S, insulin, and ascorbic acid, as needed. (second medium).
Carefully release the graft from the mold and place in a culture dish with second medium.

Example 2. Growth and Shaping Protocol

The graft is then fed, grown, and/or shaped as the collagen content increases and the fiber alignment and cross linking takes place. The graft culture media is changed periodically as needed using the second medium (Penstrep optional).

The cells in the graft are grown until the desired endpoint. In this experiment, the endpoint is determined by both visual observation and/or by product or process testing. Visual observation includes but is not limited to translucence, e.g., the tissue becoming more opaque and/or thicker. Product and process testing includes but is not limited to collagen content; tensile strength or modulus (in one or more directions, e.g., longitudinal or circumferential); suture retention (in one or more directions); histology; shrink temperature; acellular content; and thickness.

During this growth phase, various other steps may be incorporated into the protocol: mixing, detachment, and contraction.

If the culture medium needs to be mixed, the medium may be agitated, rocked, or shaken.

If collagen fiber alignment is desired, the graft may be contracted one or more times by allowing the graft to contract along the form, or by gently manually moving the graft along the form. In this example, manual manipulation was used—rings holding the tissue from contracting are moved to create slack. The cells then contract and tighten, and fibers in the tissue align.

Once the growth and shaping phase has been completed, the graft (still supported on its form) is then ready to be decellularized.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

The invention claimed is:

1. A prosthesis comprising biologically engineered extracellular matrix (ECM) tissue formed into pre-determined shape, wherein a central portion of said prosthesis is isodiametric, a first end of said prosthesis is flared, and a second end of said prosthesis is a cuff, wherein an internal diameter of said central portion is from 2 mm to 6 mm, or wherein the internal diameter is from 2 mm to 4 mm, or wherein the internal diameter is from 3 mm to 6 mm.

2. A process for making a prosthesis comprising culturing regenerative extracellular matrix (ECM) tissue, wherein said culturing occurs around a mandrel, shape or form and results in a shaped prosthesis; removing the shaped prosthesis from the mandrel, shape, or form; and shaping at least one end of said prosthesis, wherein a central portion of said prosthesis is isodiametric, a first end of said prosthesis is flared, and a second end of said prosthesis is a cuff, wherein an internal diameter of said central portion is from 2 mm to 6 mm, or wherein the internal diameter is from 2 mm to 4 mm, or wherein the internal diameter is from 3 mm to 6 mm.

3. A process for preparing a graft comprising the steps of: 1) selecting an animal tissue specimen; 2) cleaning the selected tissue to produce a cleaned tissue; 3) digesting the cleaned tissue with at least one enzyme to produce digested tissue; 4) surface-treating the digested tissue to produce surface-treated tissue; 5) forming the surface-treated tissue into a predetermined shape to produce formed tissue, wherein a central portion of said shape is isodiametric, a first end of said shape is flared, and a second end of said shape is a cuff; 6) crosslinking the formed tissue to produce crosslinked tissue; and 7) sterilizing the crosslinked tissue, wherein an internal diameter of said central portion is from 2 mm to 6 mm, or wherein the internal diameter is from 2 mm to 4 mm, or wherein the internal diameter is from 3 mm to 6 mm.

4. The process of claim 3 wherein the tissue specimen is a ureter.

5. The process of claim 3 wherein the pre-determined shape corresponds to an anastomosis site on a recipient blood vessel.

6. The prosthesis of claim 1 configured as a coronary artery bypass graft or a peripheral graft.

7. The prosthesis of claim 1, wherein a length of said prosthesis is from 20 cm to 60 cm.

8. The prosthesis of claim 1, wherein a length of said prosthesis is from 40 cm to 120 cm.

* * * * *